(12) United States Patent
Banowski et al.

(10) Patent No.: US 6,849,251 B2
(45) Date of Patent: Feb. 1, 2005

(54) ANHYDROUS ANTIPERSPIRANT COMPOSITION CONTAINING POLYSACCHARIDES

(75) Inventors: Bernhard Banowski, Duesseldorf (DE); Dieter Hengstermann, Borken (DE); Armin Wadle, Erkrath (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 255 days.

(21) Appl. No.: 10/281,482

(22) Filed: Oct. 25, 2002

(65) Prior Publication Data

US 2003/0185777 A1 Oct. 2, 2003

Related U.S. Application Data

(63) Continuation of application No. PCT/EP01/04374, filed on Apr. 18, 2001.

(30) Foreign Application Priority Data

Apr. 28, 2000 (DE) .......................................... 100 21 056

(51) Int. Cl.$^7$ ............................. A61K 7/32; A61K 7/34; A61K 7/38; A61K 7/00
(52) U.S. Cl. ............................. 424/65; 424/66; 424/68; 424/400; 424/401
(58) Field of Search ............................. 424/65, 66, 68, 424/400, 401

(56) References Cited

U.S. PATENT DOCUMENTS

| | | | |
|---|---|---|---|
| 4,202,879 A | 5/1980 | Shelton |
| 4,268,499 A | 5/1981 | Keil |
| 4,743,440 A | 5/1988 | Callingham et al. |
| 4,863,721 A | 9/1989 | Beck et al. |
| 4,937,069 A | 6/1990 | Shin |
| 5,069,897 A | 12/1991 | Orr |
| 5,176,903 A | 1/1993 | Goldberg et al. |
| 5,292,530 A | 3/1994 | McCrea et al. |
| 5,626,856 A | 5/1997 | Berndt |

FOREIGN PATENT DOCUMENTS

| | | |
|---|---|---|
| DE | 1 165 574 B1 | 3/1964 |
| EP | 0 310 252 B1 | 1/1995 |
| FR | 2 263 742 A1 | 10/1975 |
| GB | 962 919 | 7/1964 |
| GB | 2 084 872 A | 4/1982 |
| WO | WO 91/04009 A1 | 4/1991 |
| WO | WO 97/16161 A1 | 5/1997 |
| WO | WO 97/17942 A1 | 5/1997 |
| WO | WO 97/48373 A1 | 12/1997 |
| WO | WO 98/27946 A1 | 7/1998 |
| WO | WO 98/27947 A1 | 7/1998 |
| WO | WO 98/51185 A1 | 11/1998 |
| WO | WO 00/15180 | 3/2000 |
| WO | WO 01/47476 A2 | 7/2001 |
| WO | WO 01/47488 A2 | 7/2001 |

OTHER PUBLICATIONS

S. Plechner, Science and Technology: Antipersirants and Deodarants, vol. 2, pp. 373–416 (1972).
K. Laden, A Guide to Understanding Antiperspirant Formulations, Science and Technology Series:Antiperspirants and Deodorants, 2$^{nd}$ Edition, pp. 233–258 and 327–356, Marcel Dekker, Inc. New York.
Chemistry and Technology of the Cosmetics and Toiletries Industry, 2$^{nd}$ Edition, p. 326 (1996).
Kirk–Othmer Encyclopedia of Chemical Technology, vol. 3, 3$^{rd}$ Edition, John Wiley & Sons, NY, pp. 896–900 (1982).
Kirk–Othmer Encyclopedia of Chemical Technology, vol. 15, 3$^{rd}$ Edition, John Wiley & Sons, NY, pp. 439–458 (1982).
Polysaccharides, Polymers in Nature, John Wiley and Sons, NY, Chapter 6, pp. 240–328 (1980).
Industrial Gums–Polysaccharides and their Derivatives, 2$^{nd}$ Edition, Academic Press, Inc., Table of Contents (1973).
Todd et al., Volatile Silicone Fluids for Cosmetic Formulations, Cosmetics and Toiletries, vol. 91, pp. 27–32 (1976).
G. Barnett, Emollient Creams and Lotions, Cosmetics: Science and Technology, vol. 1, pp. 27–104, (1972).
Kirk–Othmer Encyclopedia of Chemical Technology, vol. 8, 3$^{rd}$ Edition, John Wiley & Sons, NY, pp. 439–458 (1979).

*Primary Examiner*—Shelley A. Dodson
(74) *Attorney, Agent, or Firm*—Stephen D. Harper; Gregory M. Hill

(57) ABSTRACT

A water-free antiperspirant composition is presented which comprises
  a) at least two particulate polysaccharides and/or polysaccharide derivatives,
  b) at least one astringent antiperspirant agent and
  c) at least one lipid component with a melting point of 30 to 150° C. in a liquid carrier material.

17 Claims, No Drawings

ANHYDROUS ANTIPERSPIRANT COMPOSITION CONTAINING POLYSACCHARIDES

CROSS REFERENCE TO RELATED APPLICATIONS

This application is a continuation under 35 U.S.C. § 365(c) and § 120 of International Application No. PCT/EP01/04374 filed Apr. 18, 2001 an under § 119 of German Patent Application No. 100 21 056.2 filed Apr. 28, 2000.

SUMMARY OF THE INVENTION

This invention relates to water-free antiperspirant compositions for applying antiperspirant agents to the skin.

BACKGROUND OF THE INVENTION

Antiperspirant compositions are known to experts in many forms. Astringent substances, for example aluminium and/or zirconium salts, are normally used as the antiperspirant agents. The compositions are marketed as sprays, roll-on preparations, sticks or creams. Formulations such as these are described in Cosmetics: Science and Technology, "Antiperspirants and Deodorants" (Ed: M. S. Balsam and E. G. Sagarin, 1972), Vol. 2, pp. 373–416 by S. Plechner and in Cosmetics Science and Technology Series: "Antiperspirants and Deodorants" (Ed: Karl Laden), 2nd Edition, pp. 233–258 and pp. 327–356.

Whereas the cosmetics market has been dominated by stick preparations in recent years, cream-like antiperspirant preparations are enjoying increasing popularity. Many antiperspirant creams, such as those described in EP 0 310 252, WO 91/04009, WO 97/16161, WO 97/17942, WO 98/51185, WO 98/27947, U.S. Pat. No. 4,863,721, U.S. Pat. No. 4,937,069 and U.S. Pat. No. 5,292,530, are formulated without water. Preparations such as these leave a pleasantly dry feeling behind on the user's skin after application. However, effective release of the particulate antiperspirant agents from such preparations is limited by comparison with water-containing formulations (cf.: Chemistry and Technology of the Cosmetics and Toiletries Industry, Ed.: D. F. Williams and W. H. Schmitt, London: Blackie, 1996, 2nd Edition, page 326), besides which the preparations often fail to leave the skin feeling fresh. In addition, water-free antiperspirant preparations based on volatile silicone oils have the disadvantage that the dispersed antiperspirant agents easily lead to visible product residues on the skin and clothing. If pressure is applied during application, "oiling out" (syneresis) often occurs and reduces the cosmetic acceptance of the preparations among users.

By contrast, water-containing emulsion-like antiperspirant creams such as those described, for example, in U.S. Pat. No. 4,268,499, WO 97/48373 and WO 98/27946 have the disadvantage that they leave an unpleasant and long-lasting feeling of wetness behind after application to the skin and are often found by users to be sticky and greasy.

The problem addressed by the present invention was to provide a water-free antiperspirant composition with improved antiperspirant performance, particularly high dermatological compatibility and optimized release of the antiperspirant agent which would be quickly and completely absorbed by the skin. Another problem addressed by the invention was to provide preferably paste-form antiperspirant compositions (creams) which would have high stability in storage without syneresis of the oil components at room temperature and high temperature stability, would not leave any oily film behind after application to the skin, would create a pleasantly velvety, dry and light impression and would be easy to wash off.

DESCRIPTION OF THE INVENTION

According to the invention, the problem stated above has been solved by a water-free antiperspirant composition which is characterized by a content of:

a) at least two particulate polysaccharides and/or polysaccharide derivatives, b) at least one astringent antiperspirant agent and c) at least one lipid component with a melting point of 30 to 150° C. in a liquid carrier material.

Water-free compositions in the context of the present invention are compositions which contain less than 5% by weight of water (not including water of crystallization), preferably less than 2% by weight of water and more particularly less than 1% by weight of water. A residual water content may emanate from the raw materials and would therefore be unavoidable.

The preparations according to the invention are fine-particle dispersions of the antiperspirant agents and the polysaccharides in a liquid carrier material. In principle, various application forms are possible, including for example roll-on preparations, sticks or paste-form/salve-like preparations (creams), although cream-like (paste-form) preparations are preferred in accordance with the invention. The polysaccharide combination provides for a particularly dry and velvety skin feel. In addition, the composition according to the invention does not leave an oily film or white residue behind on the skin or clothing, is easy to wash off, is irritation-free and is quickly absorbed by the skin.

The dispersions according to the invention are particularly suitable for application to the skin as perspiration inhibitors. In one preferred embodiment, they have a viscosity at 25° C. of at least 200 Pa.s and preferably in the range from 500 to 2,000 Pa.s (Brookfield RVF, spindle TE Helipath, 4 r.p.m., 25° C.).

The present invention also relates to a process for the production of the compositions according to the invention, characterized in that the wax and oil components are melted with stirring together with the emulsifiers, after which the powder-form constituents are incorporated with stirring and the whole is left to cool to room temperature with continuous stirring.

1. Polysaccharides

According to the invention, the polysaccharides used may be natural and synthetic polysaccharides and/or derivatives thereof, which accumulate in particulate or powder form, and homo- and heteroglycans of the usual sugar units. They may be of animal origin (for example chitin, tunicin), vegetable origin (for example starch, cellulose, alginic acid) and microbial, bacterial or synthetic origin. Such polysaccharides include the particulate the that the types which are described, for example, in "Encyclopedia of Chemical Technology", Kirk-Othmer, 3rd Edition, 1982, Vol. 3, pp. 896–900 and Vol. 15, pp. 439–458 and those described in "Polymers in Nature" (Ed.: E. A. MacGregor, C. T. Greenwood), John Wiley & Sons, 1980, Chapter 6, pp. 240–328 and in "Industrial Gums—Polysaccharides and their Derivatives" (Ed.: R. L. Whistler), 2nd Edition, Academic Press Inc. According to the invention, two particulate polysaccharides, a mixture of a polysaccharide and a polysaccharide derivative or a mixture of two polysaccharide derivatives may be used. Synthetic polysaccharides may be produced from the usual sugar units glucose, fructose, mannose, galactose, talose, gulose, allose, idose, arabinose, xylose, lyxose and ribose or mixtures thereof. Their molecular weight is preferably greater than 5,000.

The polysaccharides which stabilize the compositions against oiling out and have a stiffening effect are used in the compositions according to the invention in a total quantity of 0.1 to 30% by weight, preferably 1 to 20% by weight and more particularly 5 to 15% by weight. In order to obtain particularly fine-particle dispersions, it can be of advantage to use polysaccharides with particle sizes below 100 µm and more particularly below 50 µm.

Naturally occurring particulate polysaccharides include, for example, starch and cellulose, which are polycondensation products of D-glucose, and also inulin, a polycondensate of D-fructose. The molecular weight of the high-polymer sugars usable in accordance with the invention are normally between 5,000 and several million. They provide the compositions according to the invention with a decidedly dermatologically compatible character and a dry, velvety "rub-off".

In a preferred embodiment, the antiperspirant composition contains polysaccharides selected from the group consisting of starch and cellulose. A particularly preferred embodiment is a combination of a starch/starch derivative and a cellulose.

Starch is a storage substance of plants which occurs above all in nodules and roots, in cereal seeds and in fruit and which can be obtained in high yields from a number of plants. The polysaccharide which is insoluble in cold water and which forms a colloidal solution in boiling water can be obtained, for example, from potatoes, cassava, sweet potatoes, arrowroot, corn, cereals, rice, legumes such as, for example, peas and beans, bananas or the pulp of certain palm varieties (for example sago palm). Natural starches obtained from plants and/or chemically or physically modified starches may be used in accordance with the invention. A particularly preferred embodiment of the invention contains a hydrophobically modified starch. Hydrophobicization may be achieved, for example, by introduction of long-chain or branched side chains at one or more of the hydroxyl groups of the starch. It is normally a question here of esters, ethers or amides of the starch with $C_{1-40}$ groups. Products representing esters or ethers of the starch with carboxylic acids or fatty alcohols from natural fats and oils can be preferred. Starches esterified with one or more n-octenyl succinate residues are preferred for the purposes of the invention. A free-flowing aluminium octenyl succinate starch as marketed, for example, by National Starch under the name of "Dry Flo® Plus" is particularly advantageous. Modified crosslinked rice starches and crosslinked distarch phosphoric acid esters based on corn starch as marketed, for example, by Dr. Hauser GmbH under the names of Rice® NS, Rice® NS TC, D.S.A. 7 and P.F.A. 11 or Mais PO4® PH"B" may also be used. Starch or starch derivatives are used in the compositions according to the invention in a quantity of 0.1 to 20% by weight, preferably in a quantity of 1 to 15% by weight and more particularly in a quantity of 2 to 10% by weight.

Cellulose, an ubiquitous vegetable skeletal substance, is also suitable as a particulate polysaccharide for the purposes of the invention. It may be used in native form and also in physically or chemically modified form. Native cellulose is distinguished by particularly high dermatological compatibility and is particularly suitable for the purposes of the invention. In combination with starch, particularly hydrophobicized starch, in the compositions according to the invention, it provides for particularly good application properties and a decidedly dry and velvety skin feel and stabilizes the composition against oiling out (syneresis).

2. Lipid Components With a Melting Point of 30–150° C.

According to the invention, any fats and fat-like substances which melt at 30 to 150° C. may be used as lipid components (for a definition of lipids cf.: C D Römpp Chemie Lexikon—Version 1.0, Stuttgart/New York: Georg Thieme Verlag 1995). These include inter alia fats (triglycerides), mono- and diglycerides, waxes, fatty and wax alcohols, fatty acids, esters and/or ethers of fatty alcohols and fatty acids and also fatty acid amides or mixtures of these substances providing they melt in the stipulated range. These lipid components have structuring properties and provide the composition with the required consistency and with a particularly pleasant skin feel. They are present in the compositions according to the invention in a total quantity of 0.1 to 40% by weight, preferably 1 to 20% by weight and more particularly 5 to 15% by weight.

Fats

Fats are understood to be triacyl glycerols, i.e. the triple esters of fatty acids with glycerol. Of the triacyl glycerols, those with a melting point between 30° C. and 150° C. which contain saturated, unbranched and unsubstituted fatty acid residues are preferred lipid components. These may also be mixed esters, i.e. triple esters of glycerol with various fatty acids. So-called hydrogenated fats and oils obtained by partial hydrogenation may also be used in accordance with the invention and are particularly suitable as consistency factors. Vegetable hydrogenated fats and oils are preferred, for example hydrogenated castor oil, peanut oil, soybean oil, rape oil, rapeseed oil, cottonseed oil, soybean oil, sunflower oil, palm oil, palm kernel oil, linseed oil, almond oil, corn oil, olive oil, sesame oil, cocoa butter and coconut butter.

In a preferred embodiment, the lipid component with a melting point of 30 to 150° C. is selected from the group of triple esters of glycerol with fatty acids. Triglycerides are effective consistency factors and support the compactness of the composition. The triple esters of glycerol with $C_{18-60}$ fatty acids, more especially $C_{18-36}$ fatty acids, are particularly preferred. These include hydrogenated castor oil, a triple ester of glycerol and a hydroxystearic acid which is marketed, for example, under the name of Cutina® HR, and glycerol tristearate, glycerol tribehenate (for example Syncrowax® HRC), glycerol tripalmitate or the triglyceride mixtures known under the name of Syncrowax® HGLC.

A combination of hydrogenated castor oil and $C_{18-36}$ fatty acid triglycerides (for example Syncrowax® HGLC) is also preferred for the purposes of the invention. The combination of these triglycerides further minimizes oiling out of the composition and increases stability in storage. A combination of hydrogenated castor oil and long-chain $C_{20-40}$ fatty acids (for example Performacid® 350 Acid) has also proved to be of advantage as a consistency-providing lipid component.

Besides the triglycerides, mono- and diglycerides and mixtures thereof may also be used as lipid components providing they contain components which melt at 30 to 150° C. According to the invention, preferred glyceride mixtures include the combination of Cutina® HR (hydrogenated castor oil) and Novata® AB (mixture of $C_{12-18}$ mono-, di- and triglycerides).

Fatty Alcohols and Fatty Acids

Fatty alcohols with consistency factor properties and a melting point of 30 to 150° C. which may be used in accordance with the invention include, for example, the unbranched $C_{14-50}$ fatty alcohols, more particularly the $C_{14-30}$ fatty alcohols obtained from natural fats, oils and waxes such as, for example, myristyl alcohol, 1-pentadecanol, cetyl alcohol, 1-heptadecanol, stearyl alcohol, 1-nonadecanol, arachidyl alcohol, 1-heneicosanol, behenyl alcohol, brassidyl alcohol, lignoceryl alcohol, ceryl alcohol or myricyl alcohol. Unbranched, saturated and unsubstituted fatty alcohols are preferred for the purposes of the invention.

However, branched, saturated or unsaturated fatty alcohols may also be used in accordance with the invention providing they have the required melting point. Fatty alcohol cuts with a corresponding melting point which are obtained in the reduction of naturally occurring fats and oils may also be used in accordance with the invention.

Other suitable lipid components acting as consistency factors are $C_{12-40}$ fatty acids or mixtures thereof which melt at 30 to 150° C. These include, for example, lauric, tridecanoic, myristic, pentadecanoic, palmitic, margaric, stearic, nonadecanoic, arachic, behenic, lignoceric, cerotic, melissic, erucic and elaeostearic acid and substituted fatty acids, such as 12-hydroxystearic acid for example, and the amides or monoethanolamides of the fatty acids, this list being of purely exemplary, i.e. non-limiting, character. Among the fatty acids, a $C_{20-40}$ fatty acid mixture marketed under the name of Performacid® 350 Acid is particularly suitable.

Waxes

Waxes are understood to be natural or synthetic materials with the following properties: they are solid or fragile and hard in consistency, coarsely to finely crystalline, transparent or opaque and melt above 30° C. without decomposing. They are low in viscosity and non-stringing only slightly above their melting point and show highly temperature-dependent consistency and solubility. Waxes suitable for use in accordance with the present invention are, for example, natural vegetable waxes with a melting point of 30 to 150° C. such as, for example, candelilla wax, carnauba wax, Japan wax, espartograss wax, cork wax, guaruma wax, rice oil wax, sugar cane wax, ouricury wax, montan wax, sunflower wax, fruit waxes, such as orange waxes, lemon waxes, grapefruit wax, bayberry wax, and animal waxes such as, for example, beeswax, shellac wax, spermaceti, wool wax and uropygial fat. According to the invention, it can be of advantage to use hydrogenated waxes. Natural waxes usable in accordance with the invention also include the mineral waxes, such as ceresine and ozocerite for example, or the petrochemical waxes, for example petrolatum, paraffin waxes and microwaxes. Other suitable wax components are chemically modified waxes, more particularly the hard waxes such as, for example, montan ester waxes, sasol waxes and hydrogenated jojoba waxes. Synthetic waxes usable in accordance with the invention include, for example, wax-like polyalkylene waxes and polyethylene glycol waxes.

The wax component may also be selected from the group of esters of saturated and/or unsaturated, branched and/or unbranched alkanecarboxylic acids and saturated and/or unsaturated, branched and/or unbranched alcohols, from the group of esters of aromatic carboxylic acids, dicarboxylic acids, tricarboxylic acids and hydroxycarboxylic acids (for example 12-hydroxystearic acid) and saturated and/or unsaturated, branched and/or unbranched alcohols and also from the group of lactides of long-chain hydroxycarboxylic acids providing the wax component or all the wax components melt at 30 to 150° C. Wax components such as these include, for example, $C_{16-40}$ alkyl stearates, $C_{20-40}$ alkyl stearates (for example Kesterwachs® K82H), $C_{20-40}$ dialkyl esters of dimer acids, $C_{18-38}$ alkyl hydroxystearoyl stearates or $C_{20-40}$ alkyl erucates. Other suitable wax components which may be used with advantage are $C_{30-50}$ alkyl beeswax, tristearyl citrate, triisostearyl citrate, stearyl heptanoate, stearyl octanoate, trilauryl citrate, ethylene glycol dipalmitate, ethylene glycol distearate, ethylene glycol di(12-hydroxystearate), stearyl stearate, palmityl stearate, stearyl behenate, cetyl ester, cetearyl behenate and behenyl behenate. Silicone waxes may also be used with advantage.

3. Antiperspirant Agents

Suitable antiperspirant agents are water-soluble astringent metal salts, more particularly inorganic and organic salts of aluminium, zirconium and zinc or mixtures of these salts. By solubility in water is meant a solubility of at least 5% by weight at 20° C. In the context of the present invention, suitable antiperspirant agents are, for example, alum (KAl$(SO_4)_2 \cdot 12H_2O$), aluminium sulfate, aluminium lactate, sodium aluminium chlorohydroxylactate, aluminium chlorohydroxyallantoinate, aluminium chloride, aluminium chlorohydrate, aluminium chlorohydrex PEG, aluminium chlorohydrex PG, aluminium sulfocarbolate, aluminium dichlorohydrate, aluminium dichlorohydrex PEG, aluminium dichlorohydrex PG, aluminium sesquichlorohydrate, aluminium sesquichlorohydrex PEG, aluminium sesquichlorohydrex PG, aluminium zirconium chlorohydrates (aluminium zirconium octachlorohydrate, aluminium zirconium pentachlorohydrate, aluminium zirconium tetrachlorohydrate, aluminium zirconium trichlorohydrate), zinc chloride, zinc sulfocarbolate, zinc sulfate, zirconium chlorohydrate and aluminium zirconium chlorohydrate glycine complexes such as, for example, aluminium zirconium octachlorohydrex glycine, aluminium zirconium pentachlorohydrex glycine, aluminium zirconium tetrachlorohydrex glycine, aluminium zirconium trichlorohydrex glycine. The antiperspirant agents are used as powders in water-free creams. They are present in the compositions according to the invention in a quantity of 0.1 to 40% by weight, preferably in a quantity of 5 to 30% by weight and more particularly in a quantity of 10 to 25% by weight (based on the quantity of active substance in the composition as a whole). In a preferred embodiment, the composition contains an astringent aluminium or aluminium zirconium compound. Particularly suitable are powder-form aluminium chlorohydrates which are commercially available as Chlorhydrol®-Pulver, Reach® 501 or Micro Dry® from Reheis and aluminium zirconium chlorohydrex glycine complexes marketed by Reheis as Rezal® 36 GP Superultrafine and Rezal® 33 GP. It can also be of advantage to use aluminium zirconium pentachlorohydrates (Rezal® 67P) and an aluminium sesquichlorohydrate (Reach® 301) for the purposes of the invention.

4. Liquid Carrier Material

Suitable liquid carrier materials are nonpolar and polar liquid oil components in which the solids are homogeneously dispersed. A combination of nonpolar and polar oil component is preferred for the purposes of the invention. The nonpolar liquid oil components which normally make up most of the carrier material include silicone oils and hydrocarbons which may be linear, branched or cyclic. Suitable hydrocarbons are, for example, isohexadecane, isododecane, polydecene and mineral oils such as, for example, thickly liquid and thinly liquid paraffins. In order to guarantee good spreading of the composition on the skin, thinly liquid carrier materials are preferably used. The carrier material is present in a total quantity of 1 to 60% by weight, preferably 10 to 50% by weight and more particularly 20 to 45% by weight.

Silicones

Suitable nonpolar oil components are, in particular, silicone oils. These include, for example, dialkyl and alkylaryl siloxanes such as, for example, dimethyl polysiloxane and methylphenyl polysiloxane and alkoxylated and quaternized analogs thereof.

A preferred embodiment of the composition is characterized in that the liquid carrier material contains at least one volatile silicone component. Volatile compounds in the context of the invention are compounds which volatilize at body temperature. Suitable volatile silicones, which may be linear, branched or cyclic, are described in Todd et al. "Volatile Silicone Fluids for Cosmetics", Cosmetics and Toiletries, pp. 27–32 (1976) and are intended to be part of the disclosure of the present application. Silicones containing 3 to 7 and more particularly 4 to 6 silicon atoms are preferred for the purposes of the invention. Particularly preferred are cyclic polydimethylsiloxanes such as, for example, octamethyl cyclotetrasiloxane, decamethyl cyclopentasiloxane or dodecamethyl cyclohexasiloxane which are known as cyclomethicones. Sensorially, they contribute to a very dry skin feel. They are commercially obtainable from G.E. Silicones as Cyclomethicone D-4 and D-5, from Dow Corning Corp. as Dow Corning® 344, 345 and 244, 245, 246, from General Electric Co. as GE® 7207 and 7158. Of the linear volatile silicones, those containing 1 to 7 and preferably 2 to 3 silicon atoms are preferred. The volatile silicones are present in a quantity of 0.1 to 60% by weight, preferably in a quantity of 1 to 40% by weight and more particularly in a quantity of 10 to 35% by weight.

The composition may additionally contain nonvolatile linear silicone oils. Corresponding polyalkylsiloxanes, polyalkylaryl siloxanes and polyether siloxane copolymers are described in Cosmetics: Science and Technology, Ed.: M. Balsam and E. Sagarin, Vol. 1, 1972, pp. 27–104, in U.S. Pat. No. 4,202,879 and U.S. Pat. No. 5,069,897 and are intended to be part of the disclosure of the present application.

Hydrophilic Oils

Polar, liquid carrier components have a particularly significant influence on the performance behavior and application properties of the composition. They promote the release of the antiperspirant agent from the hydrophobic silicone or hydrocarbon base. This is an important criterion for particularly good antiperspirant performance. The polar carrier components or so-called hydrophilic oils are organic compounds which are more polar than cyclomethicones. They include, for example, liquid branched alkanols, alkanediols, polyols, ether alcohols and dialkyl ethers containing 12 to 40 carbon atoms or products of the addition of 2 to 30 moles of propylene oxide onto mono- or polyfunctional alkanols containing 3 to 20 carbon atoms and esters of carbonic acid (for example dioctyl carbonate). Also suitable for use in accordance with the invention are liquid addition products of ethylene oxide onto alkanols or polyols such as, for example, glycerol providing these products do not belong to the group of emulsifiers with an HLB value of 8 to 18 (definition: cf. o/w emulsifiers).

Suitable liquid branched alkanols are, for example, Guerbet alcohols with a single branch at the i-carbon atom, for example 2-hexyl decanol or 2-octyl dodecanol. Other suitable liquid alcohols are, for example, isotridecanol, isohexadecanol and mixtures thereof.

Suitable alkanediols are the liquid vicinal diols obtainable from $C_{12-24}$ epoxyalkanes by ring opening with water. Suitable ether alcohols are, for example, liquid mono-($C_{8-22}$)-alkylethers of glycerol, ethylene glycol, 1,2-propylene glycol or 1,2-butanediol and other $C_{12-24}$ products obtainable by ring opening of epoxyalkanes with monohydric alcohols.

Suitable dialkyl ethers are, for example, liquid alkyl methyl ethers or the di-n-alkyl ethers containing a total of 12 to 40 carbon atoms, for example di-n-octyl ether (Cetiol® OE).

Suitable liquid addition products of propylene oxide onto mono- or polyhydric alcohols are, for example, PPG-3 myristyl ether (Witconol® APM), PPG-14 butyl ether (Ucon Fluid® AP) or PPG-15 stearyl ether (Arlamol® E), PPG-9 butyl ether (Breox® B25) or PPG-10 butanediol (Macol® 57).

In a preferred embodiment, the liquid carrier material additionally contains at least one hydrophilic oil. This is preferably a branched alkanol, 2-hexyl decanol and 2-octyl dodecanol being particularly suitable. Alcohols such as these are commercially available, for example, as Eutanol® G16 and Eutanol® G. The total percentage content of the hydrophilic oil or mixtures of hydrophilic oils in the composition according to the invention is 0.1 to 30% by weight, preferably 5 to 25% by weight and more particularly 5 to 15% by weight.

5. Emulsifiers/Surfactants

Further hydrophilicization of the cream and hence optimized release of the antiperspirant agent and better removability of residues from the skin by washing are achieved by addition of emulsifiers/surfactants. Suitable surfactants are, for example, anionic and in particular nonionic surfactants. Nonionic surfactants are distinguished from anionic surfactants by better dermatological compatibility.

Nonionic Emulsifiers

Suitable nonionic emulsifiers are, for example, (1) products of the addition of up to 70 moles of ethylene oxide and/or up to 30 moles of propylene oxide onto linear fatty alcohols containing 8 to 40 carbon atoms, onto fatty acids containing 12 to 40 carbon atoms and onto alkylphenols containing 8 to 15 carbon atoms in the alkyl group;

(2) $C_{12/18}$ fatty acid monoesters and diesters of products of the addition of 1 to 50 moles of ethylene oxide onto glycerol;

(3) glycerol monoesters and diesters and sorbitan monoesters and diesters of saturated and unsaturated fatty acids containing 6 to 22 carbon atoms and ethylene oxide adducts thereof;

(4) alkyl mono- and oligoglycosides containing 8 to 22 carbon atoms in the alkyl group and ethoxylated analogs thereof;

(5) acyl glucamides;

(6) products of the addition of 15 to 60 moles of ethylene oxide onto castor oil and/or hydrogenated castor oil;

(7) polyol esters and, in particular, polyglycerol esters such as, for example, polyglycerol polyricinoleate, polyglycerol poly-12-hydroxy-stearate or polyglycerol dimerate. Mixtures of compounds from several of these classes are also suitable;

(8) products of the addition of 2 to 15 moles of ethylene oxide onto castor oil and/or hydrogenated castor oil;

(9) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

(10) wool wax alcohols;

(11) polysiloxane/polyalkyl polyether copolymers and corresponding derivatives;

(12) mixed esters of pentaerythritol, fatty acids, citric acid and fatty alcohol according to DE 1165574 PS and/or mixed esters of fatty acids containing 6 to 22 carbon atoms, methyl glucose and polyols, preferably glycerol or polyglycerol, and

(13) polyalkylene glycols.

O/W Emulsifiers

In a preferred embodiment, the composition contains at least one nonionic emulsifier with an HLB value of 8 to 18 and more particularly 13 to 18. According to the invention, it can be of advantage to use a combination of different emulsifiers with HLB values in those ranges. The total percentage content of nonionic emulsifiers with an HLB value of 8 to 18 in the composition according to the invention is 0.1 to 20% by weight, preferably 1 to 15% by weight and more particularly 5 to 10% by weight. As already mentioned, o/w emulsifiers in particular support the rapid and effective release of active principles. These emulsifiers are generally known to the expert and are listed, for example, in Kirk-Othmer, "Encyclopedia of Chemical Technology", 3rd Edition, 1979, Vol. 8, pages 913–916. According to the invention, the HLB value for ethoxylated products is calculated to the following formula: HLB=(100-L): 5, where L is the percentage by weight of lipophilic groups, i.e. fatty alkyl or fatty acyl groups, in percent by weight in the ethylene oxide adducts.

This group of emulsifiers includes inter alia products of the addition of 10 to 50 moles of ethylene oxide onto fatty alcohols, fatty acids, fatty acid alkanolamides, fatty acid monoglycerides, sorbitan fatty acid esters, methyl glucoside fatty acid esters or polyglycolether-modified polysiloxanes.

Alcohol ethoxylates with the formula $R^1O(CH_2CH_2O)_nH$ which are referred to, for example, as fatty alcohol ethoxylates or as oxoalcohol ethoxylates according to the origin of the alcohol are preferably used. In the above formula, $R^1$ is a linear or branched alkyl and/or alkenyl group containing 6 to 22 carbon atoms and n is a number of 10 to 50. Typical representatives are the adducts of on average 10 to 50 and preferably 10 to 30 mol ethylene oxide with caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol and the technical mixtures thereof obtained, for example, in the high-pressure hydrogenation of technical methyl esters based on fats and oils or aldehydes from Roelen's oxosynthesis and as monomer fraction in the dimerization of unsaturated fatty alcohols. Adducts of 10 to 40 mol ethylene oxide with technical $C_{12-18}$ fatty alcohols such as, for example, coconut oil, palm oil, palm kernel oil or tallow fatty alcohol are also suitable. In a particularly preferred embodiment, the composition according to the invention contains an emulsifier combination of an ethoxylated fatty alcohol and an ethoxylated fatty acid glyceride, for example Eumulgin® B3 and Cutina® E24.

6. Inorganic Fillers

Inorganic fillers serve not only as consistency factors, but also partly as odor absorbers. In one preferred embodiment, the composition according to the invention additionally contains at least one inorganic filler. Inorganic fillers suitable for use in accordance with the invention include inter alia metal oxides and sulfates compatible with the composition, zeolites and silicates. The inorganic filler is preferably selected from the group of silicates which advantageously support the rheological properties of the composition according to the invention. This group includes inter alia natural and synthetic silicon dioxide derivatives, for example polysilicic acids (for example Aerosil®) and hydrophobicized polysilicic acids (for example Aerosil® R974), and layer silicates, more particularly talcum, montmorillonite, kaolinite, ilite, beidellite, nontronite, saponite, hectorite, bentonite, smectite and magnesium aluminium silicates. They are used in a quantity of 0.1 to 25% by weight, preferably in a quantity of 1 to 20% by weight and more particularly in a quantity of 5 to 15% by weight.

In addition, pigments (for example titanium dioxide) may be used to support the cosmetic acceptance of the preparation among users, as may organic odor absorbers such as, for example, zinc ricinoleate, cyclodextrins and chlorophyll.

A particularly preferred embodiment of the composition according to the invention contains a) 0.1 to 25% by weight of a particulate starch, b) 0.1 to 15% by weight of a particulate cellulose, c) 0.1 to 40% by weight of an astringent antiperspirant agent, d) 0.1 to 15% by weight of a fatty acid triglyceride (melting point: 30–150° C.), e) 0.1 to 70% by weight of a volatile silicone compound, f) 0.1 to 20% by weight of a silicate, g) 0.1 to 15% by weight of an emulsifier with an HLB value of 8 to 18 and h) 0.1 to 20% by weight of a hydrophilic oil. This combination provides for further optimization of the rheological properties, the antiperspirant performance and the stability of the composition and for a reduction in residues.

7. Other Active Ingredients/Optional Components

The usual ingredients of cosmetic preparations, for example stabilizers, thickeners, humectants, lipid components (which do not melt at 30 to 150° C.), auxiliaries and additives, such as dyes and perfume oils, nanospheres, deodorizing agents, preservatives and UV absorbers, antioxidants, enzymes and also care components and refatting agents, may advantageously be incorporated as additional components in the compositions according to the invention. These additional components are preferably present in the preparation in a quantity of 0.1 to 20% by weight.

Humectants/Skin Moisturizers

In a preferred embodiment, the composition may also contain a humectant or a combination of humectants to regulate the skin moisture level. According to the invention, suitable humectants are inter alia amino acids, pyrrolidone carboxylic acid, lactic acid and salts thereof, lactitol, urea and urea derivatives, uric acid, glucosamine, creatinine, cleavage products of collagen, chitosan or chitosan salts/derivatives and, in particular, polyols and polyol derivatives (for example glycerol, diglycerol, triglycerol, ethylene glycol, propylene glycol, butylene glycol, erythritol, 1,2,6-hexanetriol, polyethylene glycols, such as PEG-4, PEG-6, PEG-7, PEG-8, PEG-9, PEG-10, PEG-12, PEG-14, PEG-16, PEG-18, PEG-20, PEG-32, PEG-40, PEG-55, PEG-60, PEG-75, PEG-90, PEG-100, PEG-135, PEG-150, PEG-180, PEG-200, PEG-240), sugars and sugar derivatives (inter alia fructose, glucose, maltose, maltitol, mannitol, inositol, sorbitol, sorbityl silanediol, sucrose, trehalose, xylose, xylitol, glucuronic acid and salts thereof), ethoxylated sorbitol (Sorbeth-6, Sorbeth-20, Sorbeth-30, Sorbeth-40), honey and hydrogenated honey, hydrogenated starch hydrolyzates and mixtures of hydrogenated wheat protein and PEG-20-acetate copolymer.

The quantity of humectants in the compositions according to the invention—where they are present—is normally 0.1 to 15% by weight, preferably 1 to 10% by weight and more particularly 2 to 8% by weight, based on the total weight of the composition.

Deodorizing Agents

Deodorizing agents suitable for use in accordance with the invention are odor maskers (for example perfume), odor absorbers or "extinguishers" (vide supra), deodorizing ion exchangers, germ inhibitors and enzyme inhibitors or a combination of these agents.

According to the invention, suitable germ-inhibiting or antimicrobial agents are, in particular, organohalogen compounds and halides, quaternary ammonium compounds, a number of plant extracts and zinc compounds. These agents include triclosan, chlorhexidine and chlorhexidine gluconate, 3,4,4'-trichlorocarbanilide, bromochlorophene, dichlorophene, chlorothymol, chloroxylenol, hexachlorophene, cloflucarban, dichloro-m-xylenol, dequalinium chloride, domiphenbromide, ammonium phenol sulfonate, benzalkonium halides, benzalkonium cetyl phosphate, benzalkonium saccharinates, benzethonium chloride, cetyl pyridinium chloride, lauryl pyridinium chloride, lauryl isoquinolinium bromide, methyl benzedonium chloride. Other suitable germ-inhibiting/antimicrobial agents are phenol, phenoxyethanol, disodium dihydroxyethyl sulfosuccinyl undecylenate, sodium bicarbonate, zinc lactate, sodium phenol sulfonate and zinc phenol sulfonate, ketoglutaric acid, terpene alcohols such as, for example, farnesol, chlorophylline/copper complexes, glycerol monoalkyl ethers, carboxylic acid esters of mono-, di- and triglycerol (for example glycerol monolaurate, diglycerol monocaprate), fatty acids and plant extracts (for example green tea and constituents of lime blossom oil).

Other antibacterial deodorizing agents are, for example, $C_{12-24}$ α-hydroxyfatty acids, α,ω-dicarboxylic acids, wool wax acids, farnesol, lantibiotics, imidazoles, flavonoids, glycoglycerolipids, sphingolipids (ceramides), sterols and other active substances which inhibit the adhesion of bacteria to the skin, for example glycosidases, lipases, proteases, carbohydrates, di- or oligosaccharide fatty acid esters, alkylated mono- or oligosaccharides and others.

The enzyme inhibitors include substances which inhibit the enzymes responsible for the decomposition of perspiration, more particularly the ester-splitting lipases, for example citric acid triethyl ester or zinc glycinate.

The quantity of deodorizing agents in the compositions according to the invention—where they are present—is 0.001 to 10% by weight, preferably 0.01 to 5% by weight and more particularly 0.1 to 3% by weight, based on the total weight of the composition.

Preservatives

The compositions according to the invention may optionally contain the usual preservatives of which the function is to prevent contamination of the product by microorganisms. Accordingly, many preservatives automatically have deodorizing properties so that some substances belong to both groups. Preservatives particularly suitable for cosmetics are, for example, benzoic acid and its derivatives (for example propyl, phenyl and butyl benzoate, ammonium, sodium, potassium and magnesium benzoate), propionic acid and its derivatives (for example ammonium, sodium, potassium and magnesium propionate), salicylic acid and its derivatives (for example sodium, potassium and magnesium salicylate), 4-hydroxybenzoic acid and esters and alkali metal salts thereof (for example methyl, ethyl, propyl, isopropyl, butyl, isobutyl, isodecyl, phenyl, phenoxyethyl and benzyl paraben, hexamidine paraben and diparaben, sodium and potassium paraben, sodium and potassium methyl paraben, potassium butyl paraben, sodium and potassium propyl paraben), alcohols and salts thereof (for example benzyl alcohol, phenethyl alcohol, phenol, potassium phenolate, phenoxyethanol, phenoxyisopropanol, o-phenylphenol), guaiacol and its derivatives, chlorhexidine and its derivatives (for example chlorhexidine diacetate, digluconate and dihydrochloride), hydantoin and its derivatives, (for example DEDM and DMDM hydantoin, DEDM hydantoin dilaurate), urea and urea derivatives (for example diazolidinyl urea, imidazolidinyl urea), ferulic acid and its derivatives (for example ethyl ferulate), sorbic acid and its derivatives (for example isopropyl sorbate, TEA sorbate, sodium, potassium and magnesium sorbate), isothiazole and oxazole derivatives (for example methyl isothiazolinone, methyl chloroisothiazolinone, dimethyl oxazolidine), quaternary ammonium compounds (for example Polyquaternium-42, Quaternium-8, Quaternium-14, Quaternium-15), carbamates (for example iodopropynyl butyl carbamate), formaldehyde and sodium formate, glutaraldehyde, glyoxal, hexamidine, dehydracetic acid, 2-bromo-2-nitropropane-1,2-diol, isopropylcresol, methyl dibromoglutaronitrile, polyaminopropyl biguanide, sodium hydroxymethyl glycinate, sodium phenol sulfonate, triclocarban, triclosan, zinc pyrithione and numerous peptide antibiotics (for example nisin).

The quantity of preservatives in the compositions according to the invention is 0.001 to 10% by weight, preferably 0.01 to 5% by weight and more particularly 0.1 to 3% by weight, based on the total weight of the composition.

Antioxidants

In a particularly advantageous embodiment, the antioxidants are selected from the group consisting of amino acids (for example glycine, histidine, tyrosine, tryptophane) and derivatives thereof, imidazole and imidazole derivatives (for example urocanic acid), peptides, such as D,L-carnosine, D-carnosine, L-carnosine and derivatives thereof (for example anserine), carotinoids, carotenes (for example α-carotene, β-carotene, lycopene) and derivatives thereof, liponic acid and derivatives thereof (for example dihydroliponic acid), aurothioglucose, propylthiouracil and other thio compounds (for example thioglycerol, thiosorbitol, thioglycolic acid, thioredoxine, glutathione, cysteine, cystine, cysteamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmol to μmol/kg), also metal chelators (for example α-hydroxyfatty acids, EDTA, EGTA, phytic acid, lactoferrine), α-hydroxy acids (for example citric acid, lactic acid, malic acid), humic acids, bile acid, bile extracts, gallic acid esters (for example propyl, octyl and dodecyl gallate), flavonoids, catechols, bilirubin, biliverdin and derivatives thereof, unsaturated fatty acids and derivatives thereof (for example χ-linolenic acid, linoleic acid, arachidonic acid, oleic acid), folic acid and derivatives thereof, hydroquinone and hydroquinone derivatives (for example arbutin), ubiquinone and ubiquinol and derivatives thereof, vitamin C and derivatives thereof (for example ascorbyl palmitate, acetate, stearate, dipalmitate, Mg ascorbyl phosphates, sodium and magnesium ascorbate, disodium ascorbyl phosphate and sulfate, potassium ascorbyl tocopheryl phosphate, chitosan ascorbate), isoascorbic acid and derivatives thereof, tocopherols and derivatives thereof (for example tocopheryl acetate, linoleate, oleate and succinate, Tocophereth-5, Tocophereth-10, Tocophereth-12, Tocophereth-18, Tocophereth-50, Tocophersolan), vitamin A and derivatives (vitamin A palmitate), the coniferyl benzoate of benzoin resin, rutin, rutinic acid and derivatives thereof, disodium rutinyl disulfate, cinnamic acid and derivatives thereof (for example ferulic acid, ethyl ferulate, caffeic acid), koji acid, chitosan glycolate and salicylate, butyl hydroxytoluene, butyl hydroxyanisole, nordihydroguaiac resin acid, trihydroxybutyrophenone, uric acid and derivatives thereof, mannose and derivatives thereof, zinc and derivatives thereof (for example ZnO, $ZnSO_4$), selenium and derivatives thereof (for example selenium methionine), stilbenes and derivatives thereof (for example stilbene oxide, trans-stilbene oxide). According to the invention, suitable derivatives (salts, esters, sugars, nucleotides, nucleosides, peptides and lipids) and mixtures of these active substances or plant extracts (for example tee tree oil, rosemary extract and rosmaric acid) containing these antioxidants may also be used.

The total quantity of antioxidants in the compositions according to the invention—where they are present—is 0.001 to 10% by weight, preferably 0.05 to 5% by weight and more particularly 0.1 to 2% by weight, based on the total weight of the preparation.

Lipophilic oil-soluble antioxidants from this group, more particularly tocopherol and its derivatives, gallic acid esters, flavonoids and carotinoids and also butyl hydroxytoluene/anisole, are preferred for the purposes of the invention. Oil-soluble UV filters and any known cosmetic or dermatological active components soluble in the lipid melt may also be present. Particularly suitable oil-soluble deodorants and preservatives are triethyl citrate and triclosan.

The compositions according to the invention may contain other cosmetic and dermatological active components such as, for example, biotin, pantothenic acid, sebostatic agents, anti-acne agents and keratolytic agents. Inflammation-inhibiting substances and substances which promote healing such as, for example, allantoin, panthenol and various plant extracts and protein hydrolyzates can also be of advantage.

EXAMPLES

The emulsifiers, oils and wax components were heated together to 85° C. until a clear melt was formed. First the polysaccharides, then the inorganic constituents and thereafter the antiperspirant agent were incorporated in the fatty phase with stirring at 85° C. The hot melt was then cooled with stirring to room temperature and then introduced into a stick tube suitable for application to the skin.

The quantities shown in the following Examples are based on % by weight active substance of the composition as a whole unless otherwise indicated.

Example 1

29.4% by weight decamethyl cyclopentasiloxane (for example Dow Corning ® 245 Fluid)
17% by weight hexyl decanol (for example Eutanol ® G16)
3% by weight hydrogenated castor oil (for example Cutina ® HR)
3% by weight Ceteareth-30 (for example Eumulgin ® B3)
6% by weight PEG-20 glyceryl stearate (for example Cutina ® E24)
8% by weight modified rice starch (for example D.S.A. 7)
2% by weight cellulose (for example Vitacel ® L 600/20 FCC)
1.5% by weight silica (Aerosil ® 200)
10% by weight talcum (for example Talkum Pharma ® G)
20% by weight aluminium chlorohydrate (for example Micro Dry ® Ultrafine)
0.1% by weight butyl hydroxytoluene

Example 2

27.4% by weight decamethyl cyclopentasiloxane (for example Dow Corning ® 245 Fluid)
17% by weight hexyl decanol (for example Eutanol ® G16)
3% by weight hydrogenated castor oil (for example Cutina ® HR)
3% by weight $C_{18-26}$ fatty acid triglyceride (for example Syncrowax ® HGLC)
3% by weight Ceteareth-30 (for example Eumulgin ® B3)
6% by weight PEG-20 glyceryl stearate (for example Cutina ® E24)
2% by weight modified rice starch (for example D.S.A. 7)
2% by weight cellulose (for example Vitacel ® L 600/20 FCC)
5% by weight aluminium starch octenyl succinate (for example Dry Flo ® Plus)
1.5% by weight silica (Aerosil ® 200)
10% by weight talcum (for example Talkum Pharma ® G)
20% by weight aluminium chlorohydrate (for example Micro Dry ® Ultrafine)
0.1% by weight tocopherol acetate

Example 3

29.3% by weight decamethyl cyclopentasiloxane (for example Dow Corning ® 245 Fluid)
17% by weight hexyl decanol (for example Eutanol ® G16)
3% by weight hydrogenated castor oil (for example Cutina ® HR)
3% by weight $C_{20-40}$ fatty acid (for example Performacid ® 350 Acid)
3% by weight Ceteareth-30 (for example Eumulgin ® B3)
6% by weight PEG-20 glyceryl stearate (for example Cutina ® E24)
2% by weight cellulose (for example Vitacel ® L 600/20 FCC)
5% by weight aluminium starch octenyl succinate (for example Dry Flo ® Plus)
1.5% by weight silica (Aerosil ® 200)
10% by weight talcum (for example Talkum Pharma ® G)
20% by weight aluminium chlorohydrate (for example Micro Dry ® Ultrafine)
0.2% by weight p-hydroxybenzoic acid propyl ester

Example 4

27.2% by weight decamethyl cyclopentasiloxane (for example Dow Corning ® 245 Fluid)
17% by weight hexyl decanol (for example Eutanol ® G16)
3% by weight hydrogenated castor oil (for example Cutina ® HR)
3% by weight $C_{20-40}$ fatty acid (for example Performacid ® 350 Acid)
3% by weight Ceteareth-30 (for example Eumulgin ® B3)
6% by weight PEG-20 glyceryl stearate (for example Cutina ® E24)
2% by weight modified rice starch (for example D.S.A. 7)
2% by weight cellulose (for example Vitacel ® L 600/20 FCC)
5% by weight aluminium starch octenyl succinate (for example Dry Flo ® Plus)
1.5% by weight silica (Aerosil ® 200)
10% by weight talcum (for example Talkum Pharma ® G)
20% by weight aluminium chlorohydrate (for example Micro Dry ® Ultrafine)
0.2% by weight benzyl alcohol
0.1% by weight butyl hydroxytoluene

Example 5

29.3% by weight decamethyl cyclopentasiloxane (for example Dow Corning ® 245 Fluid)
17% by weight hexyl decanol (for example Eutanol ® G16)
6% by weight $C_{18-36}$ fatty acid triglyceride (for example Syncrowax ® HGLC)
3% by weight Ceteareth-30 (for example Eumulgin ® B3)
6% by weight PEG-20 glyceryl stearate (for example Cutina ® E24)
2% by weight cellulose (for example Vitacel ® L 600/20 FCC)
5% by weight aluminium starch octenyl succinate (for example Dry Flo ® Plus)
1.5% by weight silica (Aerosil ® 200)
10% by weight talcum (for example Talkum Pharma ® G)
20% by weight aluminium chlorohydrate (for example Micro Dry ® Ultrafine)
0.2% by weight benzyl alcohol

Example 6

28.3% by weight decamethyl cyclopentasiloxane (for example Dow Corning ® 245 Fluid)
17% by weight 2-hexyl decanol (for example Eutanol ® G16)
3% by weight hydrogenated castor oil (for example Cutina ® HR)
3% by weight $C_{18-36}$ fatty acid triglyceride (for example Syncrowax ® HGLC)
3% by weight Ceteareth-30 (for example Eumulgin ® B3)
6% by weight PEG-20 glyceryl stearate (for example Cutina ® E24)
2% by weight cellulose (for example Vitacel ® L 600/20 FCC)
5% by weight aluminium starch octenyl succinate (for example Dry Flo ® Plus)
1.5% by weight silica (Aerosil ® 200)
10% by weight talcum (for example Talkum Pharma ® G)
20% by weight aluminium chlorohydrate (for example Micro Dry ® Ultrafine)
0.1% by weight butyl hydroxytoluene
0.1% by weight 2,4,4'-trichloro-2'-hydroxydiphenylether (for example Irgasan ® DP 300)
1.0% by weight perfume oil

Example 7

39% by weight decamethyl cyclopentasiloxane (for example Dow Corning ® 245 Fluid)
15% by weight hexyl decanol (for example Eutanol ® G16)
3% by weight hydrogenated castor oil (for example Cutina ® HR)
3% by weight Ceteareth-30 (for example Eumulgin ® B3)
6% by weight PEG-20 glyceryl stearate (for example Cutina ® E24)
2% by weight cellulose (for example Vitacel ® L 600/20 FCC)
5% by weight aluminium starch octenyl succinate (for example Dry Flo ® Plus)
2% by weight silica (Aerosil ® 200)
5% by weight talcum (for example Talkum Pharma ® G)
20% by weight aluminium chlorohydrate (for example Micro Dry ® Ultrafine)

Example 8

32.5% by weight decamethyl cyclopentasiloxane (for example Dow Corning ® 245 Fluid)
15% by weight hexyl decanol (for example Eutanol ® G16)
3% by weight hydrogenated castor oil (for example Cutina ® HR)
3% by weight Ceteareth-30 (for example Eumulgin ® B3)
6% by weight PEG-20 glyceryl stearate (for example Cutina ® E24)
4% by weight modified rice starch (for example Rice ® NS)
5% by weight aluminium starch octenyl succinate (for example Dry Flo ® Plus)
1.5% by weight silica (Aerosil ® 200)
10% by weight talcum (for example Talkum Pharma ® G)
20% by weight aluminium chlorohydrate (for example Micro Dry ® Ultrafine)

Example 9

32.5% by weight decamethyl cyclopentasiloxane (for example Dow Corning ® 245 Fluid)
15% by weight hexyl decanol (for example Eutanol ® G16)
3% by weight hydrogenated castor oil (for example Cutina ® HR)
3% by weight Ceteareth-30 (for example Eumulgin ® B3)
6% by weight PEG-20 glyceryl stearate (for example Cutina ® E24)
4% by weight crosslinked corn starch (for example Mais PO4 ® PH"B")
5% by weight aluminium starch octenyl succinate (for example Dry Flo ® Plus)
1.5% by weight silica (Aerosil ® 200)
10% by weight talcum (for example Talkum Pharma ® G)
20% by weight aluminium chlorohydrate (for example Micro Dry ® Ultrafine)

Example 10

32.5% by weight decamethyl cyclopentasiloxane (for example Dow Corning ® 245 Fluid)
17% by weight hexyl decanol (for example Eutanol ® G16)
3% by weight hydrogenated castor oil (for example Cutina ® HR)
3% by weight Ceteareth-30 (for example Eumulgin ® B3)
6% by weight PEG-20 glyceryl stearate (for example Cutina ® E24)
2% by weight cellulose (for example Vitacel ® L 600/20 FCC)
5% by weight aluminium starch octenyl succinate (for example Dry Flo ® Plus)
1.5% by weight silica (Aerosil ® 200)
10% by weight talcum (for example Talkum Pharma ® G)
20% by weight aluminium chlorohydrate (for example Micro Dry ® Ultrafine)

Example 11

28.5% by weight decamethyl cyclopentasiloxane (for example Dow Corning ® 245 Fluid)
17% by weight hexyl decanol (for example Eutanol ® G16)
6% by weight $C_{18-36}$ fatty acid triglyceride (for example Syncrowax ® HGLC)
3% by weight Ceteareth-30 (for example Eumulgin ® B3)
6% by weight PEG-20 glyceryl stearate (for example Cutina ® E24)
2% by weight cellulose (for example Vitacel ® L 600/20 FCC)
5% by weight aluminium starch octenyl succinate (for example Dry Flo ® Plus)
1.5% by weight silica (Aerosil ® 200)
10% by weight talcum (for example Talkum Pharma ® G)
20% by weight aluminium chlorohydrate (for example Micro Dry ® Ultrafine)
1.0% by weight perfume oil

Example 12

| | |
|---|---|
| 29.5% | by weight decamethyl cyclopentasiloxane (for example Dow Corning ® 245 Fluid) |
| 17% | by weight hexyl decanol (for example Eutanol ® G16) |
| 3% | by weight $C_{18-36}$ fatty acid triglyceride (for example Syncrowax ® HGLC) |
| 3% | by weight hydrogenated castor oil (for example Cutina ® HR) |
| 3% | by weight Ceteareth-30 (for example Eumulgin ® B3) |
| 6% | by weight PEG-20 glyceryl stearate (for example Cutina ® E24) |
| 2% | by weight cellulose (for example Vitacel ® L 600/20 FCC) |
| 5% | by weight aluminium starch octenyl succinate (for example Dry Flo ® Plus) |
| 1.5% | by weight silica (Aerosil ® 200) |
| 10% | by weight talcum (for example Talkum Pharma ® G) |
| 20% | by weight aluminium chlorohydrate (for example Micro Dry ® Ultrafine) |

Example 13

| | |
|---|---|
| 27.5% | by weight decamethyl cyclopentasiloxane (for example Dow Corning ® 245 Fluid) |
| 17% | by weight hexyl decanol (for example Eutanol ® G16) |
| 3% | by weight $C_{18-36}$ fatty acid triglyceride (for example Syncrowax ® HGLC) |
| 3% | by weight glyceryl tribehenate (for example Syncrowax ® HRC) |
| 3% | by weight Ceteareth-30 (for example Eumulgin ® B3) |
| 6% | by weight PEG-20 glyceryl stearate (for example Cutina ® E24) |
| 2% | by weight cellulose (for example Vitacel ® L 600/20 FCC) |
| 2% | by weight modified rice starch (for example D.S.A. 7) |
| 5% | by weight aluminium starch octenyl succinate (for example Dry Flo ® Plus) |
| 1.5% | by weight silica (Aerosil ® 200) |
| 10% | by weight talcum (for example Talkum Pharma ® G) |
| 20% | by weight aluminium chlorohydrate (for example Micro Dry ® Ultrafine) |

Example 14

| | |
|---|---|
| 36.0% | by weight decamethyl cyclopentasiloxane (for example Dow Corning ® 245 Fluid) |
| 15% | by weight hexyl decanol (for example Eutanol ® G16) |
| 1% | by weight $C_{18-36}$ fatty acid triglyceride (for example Syncrowax ® HGLC) |
| 3% | by weight hydrogenated castor oil (for example Cutina ® HR) |
| 3% | by weight Ceteareth-30 (for example Eumulgin ® B3) |
| 6% | by weight PEG-20 glyceryl stearate (for example Cutina ® E24) |
| 0.5% | by weight cellulose (for example Vitacel ® L 600/20 FCC) |
| 6% | by weight modified rice starch (for example D.S.A. 7) |
| 1.5% | by weight silica (Aerosil ® 200) |
| 8% | by weight talcum (for example Talkum Pharma ® G) |
| 20% | by weight aluminium chlorohydrate (for example Micro Dry ® Ultrafine) |

Example 15

| | |
|---|---|
| 27.5% | by weight decamethyl cyclopentasiloxane (for example Dow Corning ® 245 Fluid) |
| 17% | by weight hexyl decanol (for example Eutanol ® G16) |
| 3% | by weight glyceryl tribehenate (for example Syncrowax ® HRC) |
| 3% | by weight $C_{18-36}$ fatty acid triglyceride (for example Syncrowax ® HGLC) |
| 3% | by weight Ceteareth-30 (for example Eumulgin ® B3) |
| 6% | by weight PEG-20 glyceryl stearate (for example Cutina ® E24) |
| 2% | by weight cellulose (for example Vitacel ® L 600/20 FCC) |
| 2% | by weight modified rice starch (for example D.S.A. 7) |
| 5% | by weight aluminium starch octenyl succinate (for example Dry Flo ® Plus) |
| 1.5% | by weight silica (Aerosil ® 200) |
| 10% | by weight talcum (for example Talkum Pharma ® G) |
| 20% | by weight aluminium chlorohydrate (for example Micro Dry ® Ultrafine) |

Example 16

| | |
|---|---|
| 29.5% | by weight decamethyl cyclopentasiloxane (for example Dow Corning ® 245 Fluid) |
| 12% | by weight hexyl decanol (for example Eutanol ® G16) |
| 5% | by weight cocoglyceride (for example Novata ® AB) |
| 6% | by weight $C_{18-36}$ fatty acid triglyceride (for example Syncrowax ® HGLC) |
| 3% | by weight Ceteareth-30 (for example Eumulgin ® B3) |
| 6% | by weight PEG-20 glyceryl stearate (for example Cutina ® E24) |
| 2% | by weight cellulose (for example Vitacel ® L 600/20 FCC) |
| 5% | by weight aluminium starch octenyl succinate (for example Dry Flo ® Plus) |
| 1.5% | by weight silica (Aerosil ® 200) |
| 10% | by weight talcum (for example Talkum Pharma ® G) |
| 20% | by weight aluminium sesquichlorohydrate (for example Reach ® 301) |

Example 17

| | |
|---|---|
| 29.5% | by weight decamethyl cyclopentasiloxane (for example Dow Corning ® 245 Fluid) |
| 5% | by weight hexyl decanol (for example Eutanol ® G16) |
| 10% | by weight dicapryl ether (for example Cetiol ® OE) |
| 6% | by weight $C_{18-36}$ fatty acid triglyceride (for example Syncrowax ® HGLC) |
| 3% | by weight Ceteareth-30 (for example Eumulgin ® B3) |
| 6% | by weight PEG-20 glyceryl stearate (for example Cutina ® E24) |
| 2% | by weight cellulose (for example Vitacel ® L 600/20 FCC) |
| 5% | by weight aluminium starch octenyl succinate (for example Dry Flo ® Plus) |
| 1.5% | by weight silica (Aerosil ® 200) |
| 10% | by weight talcum (for example Talkum Pharma ® G) |
| 22% | by weight aluminium chlorohydrate (for example Micro Dry ® Ultrafine) |

Example 18

| | |
|---|---|
| 29.5% | by weight decamethyl cyclopentasiloxane (for example Dow Corning ® 245 Fluid) |
| 10% | by weight dicaprylyl ether (for example Cetiol ® OE) |
| 5% | by weight cocoglyceride (for example Novata ® AB) |
| 6% | by weight $C_{18-36}$ fatty acid triglyceride (for example Syncrowax ® HGLC) |
| 3% | by weight Ceteareth-30 (for example Eumulgin ® B3) |
| 6% | by weight PEG-20 glyceryl stearate (for example Cutina ® E24) |
| 2% | by weight cellulose (for example Vitacel ® L 600/20 FCC) |
| 5% | by weight aluminium starch octenyl succinate (for example Dry Flo ® Plus) |
| 1.5% | by weight silica (Aerosil ® 200) |

-continued

10% by weight talcum (for example Talkum Pharma ® G)
22% by weight aluminium chlorohydrate (for example Micro Dry ® Ultrafine)

Example 19

29.5% by weight decamethyl cyclopentasiloxane (for example Dow Corning ® 245 Fluid)
5% by weight hexyl decanol (for example Eutanol ® G16)
5% by weight dicaprylyl ether (for example Cetiol ® OE)
5% by weight cocoglyceride (for example Novata ® AB)
6% by weight $C_{18-36}$ fatty acid triglyceride (for example Syncrowax ® HGLC)
3% by weight Ceteareth-30 (for example Eumulgin ® B3)
6% by weight PEG-20 glyceryl stearate (for example Cutina ® E24)
2% by weight cellulose (for example Vitacel ® L 600/20 FCC)
5% by weight aluminium starch octenyl succinate (for example Dry Flo ® Plus)
1.5% by weight silica (Aerosil ® 200)
10% by weight talcum (for example Talkum Pharma ® G)
22% by weight aluminium zirconium tetrachlorohydrate (for example Rezal ® 36 GP)

Example 20

29.5% by weight decamethyl cyclopentasiloxane (for example Dow Corning ® 245 Fluid)
5% by weight hexyl decanol (for example Eutanol ® G16)
5% by weight dicaprylyl ether (for example Cetiol ® OE)
5% by weight polydecene (for example Nexbase ® 2004FG)
6% by weight $C_{18-36}$ fatty acid triglyceride (for example Syncrowax ® HGLC)
3% by weight Ceteareth-30 (for example Eumulgin ® B3)
6% by weight PEG-20 glyceryl stearate (for example Cutina ® E24)
2% by weight cellulose (for example Vitacel ® L 600/20 FCC)
5% by weight aluminium starch octenyl succinate (for example Dry Flo ® Plus)
1.5% by weight silica (Aerosil ® 200)
10% by weight talcum (for example Talkum Pharma ® G)
22% by weight aluminium chlorohydrate (for example Micro Dry ® Ultrafine)

Example 21

28.5% by weight decamethyl cyclopentasiloxane (for example Dow Corning ® 245 Fluid)
5% by weight hexyl decanol (for example Eutanol ® G16)
5% by weight dicaprylyl ether (for example Cetiol ® OE)
5% by weight cocoglyceride (for example Novata ® AB)
6% by weight $C_{18-36}$ fatty acid triglyceride (for example Syncrowax ® HGLC)
3% by weight Ceteareth-30 (for example Eumulgin ® B3)
6% by weight PEG-20 glyceryl stearate (for example Cutina ® E24)
3% by weight cellulose (for example Vitacel ® L 600/20 FCC)
5% by weight aluminium starch octenyl succinate (for example Dry Flo ® Plus)
1.5% by weight silica (Aerosil ® 200)
10% by weight talcum (for example Talkum Pharma ® G)
22% by weight aluminium chlorohydrate (for example Micro Dry ® Ultrafine)

Example 22

29% by weight decamethyl cyclopentasiloxane (for example Dow Corning ® 245 Fluid)
5% by weight hexyl decanol (for example Eutanol ® G16)
5% by weight dicaprylyl ether (for example Cetiol ® OE)
5% by weight polydecene (for example Nexbase ® 2004FG)
6% by weight $C_{18-36}$ fatty acid triglyceride (for example Syncrowax ® HGLC)
3% by weight Ceteareth-30 (for example Eumulgin ® B3)
6% by weight PEG-20 glyceryl stearate (for example Cutina ® E24)
3% by weight cellulose (for example Vitacel ® L 600/20 FCC)
5% by weight aluminium starch octenyl succinate (for example Dry Flo ® Plus)
10% by weight talcum (for example Talkum Pharma ® G)
22% by weight aluminium chlorohydrate (for example Micro Dry ® Ultrafine)
1% by weight perfume oil

Example 23

29.5% by weight decamethyl cyclopentasiloxane (for example Dow Corning ® 245 Fluid)
5% by weight dicapryl ether (for example Cetiol ® OE)
5% by weight cocoglyceride (for example Novata ® AB)
5% by weight polydecene (for example Nexbase ® 2004FG)
6% by weight $C_{18-36}$ fatty acid triglyceride (for example Syncrowax ® HGLC)
3% by weight Ceteareth-30 (for example Eumulgin ® B3)
6% by weight PEG-20 glyceryl stearate (for example Cutina ® E24)
2% by weight cellulose (for example Vitacel ® L 600/20 FCC)
5% by weight aluminium starch octenyl succinate (for example Dry Flo ® Plus)
10% by weight talcum (for example Talkum Pharma ® G)
1.5% by weight silica (for example Aerosil ® 200)
22% by weight aluminium chlorohydrate (for example Micro Dry ® Ultrafine)

Example 24

28.5% by weight decamethyl cyclopentasiloxane (for example Dow Corning ® 245 Fluid)
5% by weight hexyl decanol (for example Eutanol ® G16)
5% by weight cocoglyceride (for example Novata ® AB)
5% by weight polydecene (for example Nexbase ® 2004FG)
6% by weight $C_{18-36}$ fatty acid triglyceride (for example Syncrowax ® HGLC)
3% by weight Ceteareth-30 (for example Eumulgin ® B3)
6% by weight PEG-20 glyceryl stearate (for example Cutina ® E24)
2% by weight cellulose (for example Vitacel ® L 600/20 FCC)
5% by weight aluminium starch octenyl succinate (for example Dry Flo ® Plus)
1.5% by weight silica (Aerosil ® 200)
10% by weight talcum (for example Talkum Pharma ® G)
21% by weight aluminium chlorohydrate (for example Micro Dry ® Ultrafine)
1% by weight perfume oil

Example 25

27.5% by weight decamethyl cyclopentasiloxane (for example Dow Corning ® 245 Fluid)
5% by weight hexyl decanol (for example Eutanol ® G16)
5% by weight dicaprylyl ether (for example Cetiol ® OE)
5% by weight cocoglyceride (for example Novata ® AB)

-continued

6% by weight C$_{18-36}$ fatty acid triglyceride (for example Syncrowax ® HGLC)
3% by weight Ceteareth-30 (for example Eumulgin ® B3)
6% by weight PEG-20 glyceryl stearate (for example Cutina ® E24)
2% by weight cellulose (for example Vitacel ® L 600/20 FCC)
2% by weight modified rice starch (for example D.S.A. 7)
5% by weight aluminium starch octenyl succinate (for example Dry Flo ® Plus)
1.5% by weight silica (for example Aerosil ® 200)
10% by weight talcum (for example Talkum Pharma ® G)
22% by weight aluminium chlorohydrate (for example Micro Dry ® Ultrafine)

Example 26

27.5% by weight decamethyl cyclopentasiloxane (for example Dow Corning ® 245 Fluid)
5% by weight octyl decanol (for example Eutanol ® G)
5% by weight cocoglyceride (for example Novata ® AB)
5% by weight polydecene (for example Nexbase ® 2004FG)
6% by weight C$_{18-36}$ fatty acid triglyceride (for example Syncrowax ® HGLC)
3% by weight Ceteareth-30 (for example Eumulgin ® B3)
6% by weight PEG-20 glyceryl stearate (for example Cutina ® E24)
2% by weight cellulose (for example Vitacel ® L 600/20 FCC)
2% by weight modified rice starch (for example D.S.A. 7)
5% by weight aluminium starch octenyl succinate (for example Dry Flo ® Plus)
1.5% by weight silica (Aerosil ® 200)
10% by weight talcum (for example Talkum Pharma ® G)
22% by weight aluminium chlorohydrate (for example Micro Dry ® Ultrafine)

Example 27

27.5% by weight decamethyl cyclopentasiloxane (for example Dow Corning ® 245 Fluid)
5% by weight dicaprylyl ether (for example Cetiol ® OE)
5% by weight cocoglyceride (for example Novata ® AB)
5% by weight polydecene (for example Nexbase ® 2004FG)
6% by weight C$_{18-36}$ fatty acid triglyceride (for example Syncrowax ® HGLC)
3% by weight Ceteareth-30 (for example Eumulgin ® B3)
6% by weight PEG-20 glyceryl stearate (for example Cutina ® E24)
2% by weight cellulose (for example Vitacel ® L 600/20 FCC)
2% by weight modified rice starch (for example D.S.A. 7)
5% by weight aluminium starch octenyl succinate (for example Dry Flo ® Plus)
1.5% by weight silica (for example Aerosil ® 200)
10% by weight talcum (for example Talkum Pharma ® G)
22% by weight aluminium chlorohydrate (for example Micro Dry ® Ultrafine)

Example 28

29.5% by weight decamethyl cyclopentasiloxane (for example Dow Corning ® 245 Fluid)
5% by weight hexyl decanol (for example Eutanol ® G16)
5% by weight dicaprylyl ether (for example Cetiol ® OE)
5% by weight cocoglyceride (for example Novata ® AB)
6% by weight C$_{18-36}$ fatty acid triglyceride (for example Syncrowax ® HGLC)
3% by weight Ceteareth-30 (for example Eumulgin ® B3)
6% by weight PEG-20 glyceryl stearate (for example Cutina ® E24)
2% by weight cellulose (for example Vitacel ® L 600/20 FCC)

5% by weight aluminium starch octenyl succinate (for example Dry Flo ® Plus)
1.5% by weight silica (for example Aerosil ® R972)
10% by weight talcum (for example Talkum Pharma ® G)
22% by weight aluminium chlorohydrate (for example Micro Dry ® Ultrafine)

Example 29

27.5% by weight decamethyl cyclopentasiloxane (for example Dow Corning ® 245 Fluid)
5% by weight dicaprylyl ether (for example Cetiol ® OE)
5% by weight cocoglyceride (for example Novata ® AB)
5% by weight polydecene (for example Nexbase ® 2004FG)
6% by weight C$_{18-36}$ fatty acid triglyceride (for example Syncrowax ® HGLC)
3% by weight Ceteareth-30 (for example Eumulgin ® B3)
6% by weight PEG-20 glyceryl stearate (for example Cutina ® E24)
2% by weight cellulose (for example Vitacel ® L 600/20 FCC)
2% by weight modified rice starch (for example D.S.A. 7)
5% by weight aluminium starch octenyl succinate (for example Dry Flo ® Plus)
1.5% by weight silica (for example Aerosil ® R972)
10% by weight talcum (for example Talkum Pharma ® G)
22% by weight aluminium chlorohydrate (for example Micro Dry ® Ultrafine)

Example 30

29.5% by weight decamethyl cyclopentasiloxane (for example Dow Corning ® 245 Fluid)
5% by weight hexyl decanol (for example Eutanol ® G16)
5% by weight dicaprylyl ether (for example Cetiol ® OE)
5% by weight cocoglyceride (for example Novata ® AB)
6% by weight hydrogenated castor oil (for example Cutina ® HR)
3% by weight Ceteareth-30 (for example Eumulgin ® B3)
6% by weight PEG-20 glyceryl stearate (for example Cutina ® E24)
2% by weight cellulose (for example Vitacel ® L 600/20 FCC)
5% by weight aluminium starch octenyl succinate (for example Dry Flo ® Plus)
1.5% by weight silica (for example Aerosil ® 200)
10% by weight talcum (for example Talkum Pharma ® G)
22% by weight aluminium chlorohydrate (for example Micro Dry ® Ultrafine)

Example 31

29.5% by weight decamethyl cyclopentasiloxane (for example Dow Corning ® 245 Fluid)
5% by weight dicaprylyl ether (for example Cetiol ® OE)
5% by weight dioctyl carbonate (for example Cetiol ® CC)
5% by weight cocoglyceride (for example Novata ® AB)
6% by weight C$_{18-36}$ fatty acid triglyceride (for example Syncrowax ® HGLC)
3% by weight Ceteareth-30 (for example Eumulgin ® B3)
6% by weight PEG-20 glyceryl stearate (for example Cutina ® E24)
2% by weight cellulose (for example Vitacel ® L 600/20 FCC)
5% by weight aluminium starch octenyl succinate (for example Dry Flo ® Plus)
1.5% by weight silica (for example Aerosil ® 200)
10% by weight talcum (for example Talkum Pharma ® G)
22% by weight aluminium chlorohydrate (for example Micro Dry ® Ultrafine)

Example 32

29.5% by weight decamethyl cyclopentasiloxane (for example Dow Corning ® 245 Fluid)
17% by weight octyl decanol (for example Eutanol ® G)
3% by weight $C_{18-36}$ fatty acid triglyceride (for example Syncrowax ® HGLC)
3% by weight hydrogenated castor oil (for example Cutina ® HR)
3% by weight Ceteareth-30 (for example Eumulgin ® B3)
6% by weight PEG-20 glyceryl stearate (for example Cutina ® E24)
2% by weight cellulose (for example Vitacel ® L 600/20 FCC)
5% by weight aluminium starch octenyl succinate (for example Dry Flo ® Plus)
1.5% by weight silica (for example Aerosil ® 200)
10% by weight talcum (for example Talkum Pharma ® G)
20% by weight aluminium chlorohydrate (for example Micro Dry ® Ultrafine)

Example 33

29.5% by weight decamethyl cyclopentasiloxane (for example Dow Corning ® 245 Fluid)
5% by weight octyl decanol (for example Eutanol ® G)
5% by weight dicaprylyl ether (for example Cetiol ® OE)
5% by weight polydecene (for example Nexbase ® 2004FG)
6% by weight $C_{18-36}$ fatty acid triglyceride (for example Syncrowax ® HGLC)
3% by weight Ceteareth-30 (for example Eumulgin ® B3)
6% by weight PEG-20 glyceryl stearate (for example Cutina ® E24)
2% by weight cellulose (for example Vitacel ® L 600/20 FCC)
5% by weight aluminium starch octenyl succinate (for example Dry Flo ® Plus)
1.5% by weight silica (for example Aerosil ® 200)
10% by weight talcum (for example Talkum Pharma ® G)
22% by weight aluminium chlorohydrate (for example Micro Dry ® Ultrafine)

Example 34

29% by weight decamethyl cyclopentasiloxane (for example Dow Corning ® 245 Fluid)
5% by weight hexyl decanol (for example Eutanol ® G16)
5% by weight cocoglyceride (for example Novata ® AB)
5% by weight polydecene (for example Nexbase ® 2004FG)
6% by weight $C_{18-36}$ fatty acid triglyceride (for example Syncrowax ® HGLC)
3% by weight Ceteareth-30 (for example Eumulgin ® B3)
6% by weight PEG-20 glyceryl stearate (for example Cutina ® E24)
2% by weight cellulose (for example Vitacel ® L 600/20 FCC)
5% by weight aluminium starch octenyl succinate (for example Dry Flo ® Plus)
11% by weight talcum (for example Talkum Pharma ® G)
22% by weight aluminium chlorohydrate (for example Micro Dry ® Ultrafine)
1% by weight perfume oil

Example 35

28% by weight decamethyl cyclopentasiloxane (for example Dow Corning ® 245 Fluid)
5% by weight octyl decanol (for example Eutanol ® G)
5% by weight cocoglyceride (for example Novata ® AB)
5% by weight polydecene (for example Nexbase ® 2004FG)
6% by weight $C_{18-36}$ fatty acid triglyceride (for example Syncrowax ® HGLC)
3% by weight Ceteareth-30 (for example Eumulgin ® B3)
6% by weight PEG-20 glyceryl stearate (for example Cutina ® E24)
2% by weight cellulose (for example Vitacel ® L 600/20 FCC)
2% by weight modified rice starch (for example D.S.A. 7)
5% by weight aluminium starch octenyl succinate (for example Dry Flo ® Plus)
11% by weight talcum (for example Talkum Pharma ® G)
22% by weight aluminium chlorohydrate (for example Micro Dry ® Ultrafine)

Comparison Example 32.0% by weight decamethyl cyclopentasiloxane (for example Dow Corning ® 245 Fluid)
15% by weight hexyl decanol (for example Eutanol ® G)
3% by weight hydrogenated castor oil (for example Cutina ® HR)
3% by weight Ceteareth-30 (for example Eumulgin ® B3)
6% by weight PEG-20 glyceryl stearate (for example Cutina ® E24)
6% by weight cellulose (for example Vitacel ® L 600/20 FCC)
20% by weight aluminium chlorohydrate (for example Micro Dry ® Ultrafine)
15% by weight talcum (for example Talkum Pharma ® G)

All the formulations according to the invention left a dry, velvety feeling behind on the user's skin and were quickly absorbed. The formulation of the Comparison Example (with only one polysaccharide) was judged by the users to be sensorially less satisfactory and has stability disadvantages.

H 4411 PCT/US          45          PATENT

Appendix

1) Aerosil® 200
   INCI: Silica
   Manufacturer: Degussa-Hüls

H 4411 PCT/US                 46              PATENT

2) Aerosil® R 974
   INCI: Silica Dimethyl Silylate
   Manufacturer: Degussa-Hüls 3) Cab-O-Sil® M5
   INCI: Silica
   Manufacturer: Cabot (Biesterfeld)

4) Cetiol® CC
   INCI: Dioctylcarbonat
   Manufacturer: Cognis Deutschland GmbH (Henkel)

5) Cetiol® OE
   INCI: Dicapryl Ether
   Manufacturer: Cognis Deutschland GmbH (Henkel)

6) Cetiol® PGL
   INCI: Hexyldecanol, Hexydecyl Laurate
   Manufacturer: Cognis Deutschland GmbH (Henkel)

7) Cutina® E24
   INCI: PEG-20 Glyceryl Stearate
   Manufacturer: Cognis Deutschland GmbH (Henkel)

8) Cutina® HR
   INCI: Hydrogenated Castor Oil
   Manufacturer: Cognis Deutschland GmbH (Henkel)

9) Dow Corning® DC245
   INCI: Cyclomethicone

Manufacturer: Dow Corning

10) D.S.A. 7
   Modified corn starch, non-crosslinked
   Manufacturer: Dr. Hauser GmbH 11) Dry Flo® Plus
   INCI: Aluminium Octenyl Succinate
   Manufacturer: National starch 12) Eumulgin® B3
   INCI: Ceteareth-30
   Manufacturer: Cognis Deutschland GmbH (Henkel)

13) Eutanol® G16
   INCI: Hexyldecanol
   Manufacturer: Cognis Deutschland GmbH (Henkel)

14) Eutanol® G
   INCI: Octyldodecanol
   Manufacturer: Cognis Deutschland GmbH (Henkel)

15) Lorol® C18
   INCI: Stearyl Alcohol
   Manufacturer: Cognis Deutschland GmbH (Henkel)

16) Mais PO4® PH"B"
   INCI: Distarch Phosphate
   Manufacturer: Dr. Hauser GmbH

H 4411 PCT/US     48     PATENT

17) Nexbase® 2004 FG
    INCI: Polydecene
    Manufacturer: Fortum (Nynäs GmbH)

18) Novata® AB
    INCI: Cocoglycerides
    Manufacturer: Cognis Deutschland GmbH (Henkel)

19) Micro Dry® UF
    INCI: Aluminium Chlorohydrate
    Manufacturer: Reheis

20) Performacid® 350 Acid
    INCI: $C_{20}$-$C_{40}$ Acid (and) Polyethylene
    Manufacturer: New Phase Technologies 21) Reach® 301
    INCI: Aluminiumsesquichlorohydrate
    Manufacturer: Reheis 22) Rezal® 36GP
    INCI: Aluminium-Zirconium Tetrachlorohydrex Glycine
    Manufacturer: Reheis 23) Rice® NS
    Crosslinked starch
    Manufacturer: Dr. Hauser GmbH 24) Syncrowax® HGLC
    INCI: $C_{18}$-$C_{36}$ acid triglyceride Manufacturer: Croda 25) Syncrowax® HRC
   INCI: Glyceryl Tribehenate
   Manufacturer: Croda 26) Talkum Pharma® G
   INCI: Talc
   Manufacturer: China National Metals & Minerals (Erbslöh)

27) Ucon® AP
   INCI: PPG-14 Butyl ether
   Manufacturer: Amerchol (Union Carbide)

28) Vitacel® L 600/20 FCC
   Cellulose powder
   Manufacturer: J. Rettenmaier & Söhne

What is claimed
1. A water-free antiperspirant composition comprising:
   a) 0.1 to 15% by weight of at least one particulate polysaccharide selected from the group consisting of cellulose and cellulose derivatives;
   b) 0.1 to 25% by weight, of at least one particulate polysaccharide selected from the group consisting of starch and starch derivatives;
   c) at least one astringent antiperspirant agent and
   d) at least one lipid component with a melting point of 30 to 150° C. said component being selected from the group consisting of the triple esters of glycerol with fatty acids, in a liquid carrier material.

2. The composition of claim 1, wherein the starch is hydrophobically modified.

3. The composition of claim 1, wherein the antiperspirant agent is an astringent aluminium and/or aluminium zirconium compound.

4. The composition of claim 3 wherein she antiperspirant agent is present in a quantity of from 0.1 to 40% by weight.

5. The composition of claim 1 wherein the lipid component is present in a quantity of from 0.1 to 40% by weight.

6. The composition of claim 1, wherein the liquid carrier material contains a volatile silicone compound.

7. The composition of claim 6 wherein the liquid carrier material is present in a quantity of from 1 to 60% by weight.

8. The composition of claim 7, wherein the liquid cater material additionally contains at least one hydrophilic oil.

9. The composition of claim 1, wherein at least one inorganic filler is additionally present.

10. The composition of claim 9, wherein the inorganic filler is present in a quantity of from 0.1 to 25% by weight.

11. The composition of claim 10, wherein the inorganic filler is selected from the group of silicates.

12. The composition of claim 1, wherein said composition additionally contains at least one nonionic emulsifier with an HLB value of 8 to 18.

13. The composition of claim 12 wherein the emulsifier is present in a quantity of from 0.1 to 20% by weight.

14. The composition of claim 13, wherein said composition has a viscosity at 25° C. of at least 200 Pa.s.

15. The composition of claim 1, wherein said composition comprises the following components:
   a) 0.1 to 25% by weight of a particulate starch,
   b) 0.1 to 15% by weight of a particulate cellulose,
   c) 0.1 to 40% by weigh; of an astringent antiperspirant agent,
   d) 0.1 to 0.15% by weight of a fatty acid triglyceride (melting point: 30–150° C.),
   e) 0.1 to 70% by weight of a volatile silicone compound,
   f) 0.1 to 20% by weigh; of a silicate,
   g) 0.1 to 15% by weigh; of an emulsifier with an HLB value of 8 to 18 and
   h) 0.1 to 0.20% by weight of a hydrophilic oil.

16. A method of inhibiting skin perspiration which comprises applying to said skin a water-free antiperspirant composition comprising
   a) 0.1 to 0 15%, by weight, of at least one particulate polysaccharide selected from the group consisting of cellulose and cellulose derivatives;
   b) 0.1 to 25% by weight, of at least one particulate polysaccharide selected from the group consisting of starch and starch derivatives;
   c) at least one astringent antiperspirant agent and
   d) at least one lipid component with a melting point of 30 to 150° C. said component being selected from the group consisting of the triple esters of glycerol with fatty acids, in a liquid carrier material.

17. A process for the production of the composition of claim 1 which comprises
   a) hearing and mixing the emulsifiers, oils and wax components,
   b) incorporating with stirring the poly saccharides, inorganic constituents and the antiperspirant agent and
   c) cooling the mixture with continuous stirring to room temperature.

* * * * *

UNITED STATES PATENT AND TRADEMARK OFFICE
CERTIFICATE OF CORRECTION

PATENT NO. : 6,849,251 B2
DATED : February 1, 2005
INVENTOR(S) : Banowski et al.

It is certified that error appears in the above-identified patent and that said Letters Patent is hereby corrected as shown below:

Column 35,
Line 12, after "150° C." insert a -- , --.
Line 20, delete "she" and insert -- the --.
Line 28, delete "cater" and insert -- carried --.

Column 36,
Lines 6, 11 and 13, delete "weigh" and insert -- weight --.
Line 15, delete "0.20%" and insert -- 20% --.
Line 23, after "25%" insert a -- , --.
Line 28, after "150° C." insert a -- , --.
Line 34, delete "hearing" and insert -- heating --.
Line 36, delete "poly saccharides" and insert -- polysaccharides --.

Signed and Sealed this

Fourth Day of October, 2005

JON W. DUDAS
*Director of the United States Patent and Trademark Office*